United States Patent
Linguraru et al.

(10) Patent No.: US 9,883,817 B2
(45) Date of Patent: Feb. 6, 2018

(54) MANAGEMENT, ASSESSMENT AND TREATMENT PLANNING FOR INFLAMMATORY BOWEL DISEASE

(71) Applicant: Children's National Medical Center, Washington, DC (US)

(72) Inventors: Marius George Linguraru, Washington, DC (US); Juan Jose Cerrolaza, Washington, DC (US); Nabile M Safdar, Laurel, MD (US); Raymond Sze, McLean, VA (US); Laurie S Conklin, Columbia, MD (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 223 days.

(21) Appl. No.: 14/549,243

(22) Filed: Nov. 20, 2014

(65) Prior Publication Data
US 2015/0141800 A1    May 21, 2015

Related U.S. Application Data

(60) Provisional application No. 61/906,559, filed on Nov. 20, 2013.

(51) Int. Cl.
*A61B 5/05* (2006.01)
*A61B 5/055* (2006.01)
(Continued)

(52) U.S. Cl.
CPC ............ *A61B 5/055* (2013.01); *A61B 5/4255* (2013.01); *G06T 7/0012* (2013.01); *G06T 7/20* (2013.01);
(Continued)

(58) Field of Classification Search
CPC combination set(s) only.
See application file for complete search history.

(56) References Cited

PUBLICATIONS

Hamy V. et al. (2013) Respiratory Motion Correction in Dynamic-MRI: Application to Small Bowel Motility Quantification during Free Breathing. In: Mori K., Sakuma I., Sato Y., Barillot C., Navab N. (eds) Medical Image Computing and Computer-Assisted Intervention—MICCAI 2013. MICCAI 2013. Lecture Notes in Computer Science, vol. 8150. Springer.*

(Continued)

*Primary Examiner* — Ellsworth Weatherby
(74) *Attorney, Agent, or Firm* — Oblon, McClelland, Maier & Neustadt, L.L.P.

(57) ABSTRACT

Discussed herein is an image processing device and a corresponding method for assessing inflammatory bowel diseases. A plurality of dynamic MRI sequence of images of a bowel that include peristalsis information of the bowel and static MRI image(s) of the bowel that identify at areas of inflammation, stenosis, and increased mural thickness of the bowel are processed. A displacement of the bowel caused by respiration of the patient is conducted on the dynamic MRI sequences by performing a non-rigid registration. A peristaltic activity is determined by performing motion flow analysis on the dynamic sequences of images. A peristaltic activity of the static MRI image(s) based on a weighted sum of two closest dynamic MRI sequences of images is computed and the static image is combined with the closest dynamic MRI sequence of images by performing a multimodal registration.

23 Claims, 6 Drawing Sheets
(3 of 6 Drawing Sheet(s) Filed in Color)

(51) Int. Cl.
  *A61B 5/00* (2006.01)
  *G06T 7/00* (2017.01)
  *G06T 7/20* (2017.01)
  *G06T 7/38* (2017.01)

(52) U.S. Cl.
  CPC ............ *G06T 7/38* (2017.01); *A61B 2576/02* (2013.01); *G06T 2207/10088* (2013.01); *G06T 2207/30028* (2013.01)

(56) References Cited

PUBLICATIONS

Odille et al., Quantitative assessment of small bowel motility by nonrigid registration of dynamic MR images, Proc. Intl. Soc. Mag. Reson. Med. 19 (2011).*
Ailiani et al., Quantitative Analysis of Peristaltic and Segmental Motion In Vivo in the Rat Small Intestine Using Dynamic MRI, Magnetic Resonance in Medicine 62:116-126 (2009).*
Pupillo et al., Assessment of inflammatory activity in Crohn's disease by means of dynamic contrast-enhanced MRI, Radiol med (2007) 112:798-809.*
Valentin Hamy et al., "Respiratory Motion Correction in Dynamic-MRI: Application to Small Bowel Motility Quantification During Free Breathing", MICCAI 2013, Part II, LNCS 8150, 2013, pp. 132-140.
Freddy Odille et al., "Quantitative Assessment of Small Bowel Motility by Nonrigid Registration of Dynamic MR Images", Magnetic Resonance in Medicine, 68, 2012, pp. 783-793.
Berthold K.P. Horn et al., "Determining Optical Flow", Artificial Intelligence, 17, 1981, pp. 185-203.
William R. Best et al., "Development of a Crohn's Disease Activity Index", Gastroenterology, 70, 1976, pp. 439-444.
Aser Farghal et al., "Developing a New Measure of Small Bowel Peristalsis with Dynamic MR: A Proof of Concept Study", Acta Radiologica 2012, 53, 2012, 9 pages.
Alex Menys et al., "Quantified Terminal Ileal Motility During MR Enterography as a Potential Biomarker of Crohn's Disease Activity: A Preliminary Study", Eur Radiol., Gastrointestinal, 2012, 8 pages.
Johannes M. Froehlich et al., "MR Motility Imaging in Crohn's Disease Improves Lesion Detection Compared with Standard MR Imaging", Eur Radiol., Gastrointestinal, 20, 2010, pp. 1945-1951.
Michael J. Steward et al., Non-perforating Small Bowel Crohn's Disease Assessed by MRI Enterography: Derivation and Histopathological Validation of an MR-based Activity Index, European Journal of Radiology, 81, 2012, pp. 2080-2088.
Peter J. Schüffler et al., "A Model Development Pipeline for Crohn's Disease Severity Assessment from Magnetic Resonance Images", Abdominal Imaging 2013, LNCS 8198, 2013, 10 pages.

* cited by examiner

MANAGEMENT, ASSESSMENT AND TREATMENT PLANNING FOR INFLAMMATORY BOWEL DISEASE

INCORPORATION BY REFERENCE

This disclosure claims the benefit of U.S. Provisional Application No. 61/906,559, filed on Nov. 20, 2013, the disclosure of which is incorporated herein by reference in its entirety.

FIELD OF INVENTION

The present disclosure relates to assessment and characterization of inflammatory bowel disease such as Crohn's disease, ulcerative colitis, collagenous colitis, lymphocytic colitis and the like, based on new multimodal magnetic resonance imaging biomarkers. Specifically, a management, assessment and treatment planning (MAP) system described herein merges anatomical and structural information of the small bowel with quantitation of peristaltic activity in order to facilitate quantitative, accurate and objective diagnosis, longitudinal follow up, and assessment of patients with bowel diseases.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Clinical identification of inflammatory bowel disease is performed based on clinical symptoms (which are largely subjective), with confirmation using an endoscopy and/or colonoscopy with tissue biopsy. However, these techniques have limited access to areas of the small bowel, carry a risk of perforation, and don't provide an accurate assessment of disease severity. While magnetic resonance enterography is one of the best non-invasive imaging technologies for evaluating inflammatory bowel disease, its interpretation remains subjective and variable, especially when it comes to assessing the severity of inflammatory bowel disease in the small bowel. Thus this invention addresses the creation of computer-aided diagnosis and decision support systems to assess presence and severity of inflammatory bowel disease.

Crohn's Disease Activity Index (CDAI), as described by Best et al. in "Development of a Crohn's Disease Activity Index", National Cooperative Crohn's Disease Study, Gastroenterology 70, 439-444 (1976), and incorporated by reference in its entirety, is a symptom-based score used to quantify the symptoms of patients with Crohn's disease. The CDAI is a single index that is used for assessing a variety of therapies in Crohn's disease. Specifically, CDAI combines eight different clinical variables in its computation and is usually based on averaging scores over the course of a week. Thus, due to its dependency on a large time-interval (such as a week or the like), the use of the CDAI index has been limited to the realm of clinical trials. Additionally, a widely acknowledged limitation of the CDAI technique is lack of specificity, and as a result, experts support the notion of replacing the CDAI technique to quantify Crohn's disease by a robust alternative.

A non-invasive technique for developing disease indexes, proposed by Steward et al. in "Non-Perforating Small Bowel Crohn's Disease Assessed by MRI Enterography: Derivation and Histopathological Validation of an MR-based Activity Index", European Journal of Radiology, v. 81 (9), 2080-2088 (2012), and incorporated herein by reference in its entirety, is a magnetic resonance based index of luminal small bowel Crohn's disease activity. However, in the technique used by Stewart, only breath-hold examinations are considered, and no motility information is included in the formulation of the disease index that uses only manual measurements of the mural thickness.

A technique to quantify different grades of bowel motility in patients using non-rigid registration and intensity changes was proposed by Odille et al. in "Quantitative Assessment of Small Bowel Motility by Non-rigid Registration of Dynamic MR Images", Magnetic Resonance in Medicine vol. 68. 783-793 (2012), and is incorporated by reference in its entirety. However, in the technique proposed by Odille, only breath-hold cine magnetic resonance imaging was considered thereby limiting the potential applicability of the method. Furthermore, the proposed technique did not provide any structural information of the bowel.

In a similar work, proposed by Hamy et al. in "Respiratory Motion Correction in Dynamic-MRI: Application to Small Bowel Motility Quantification during Free Breathing", Medical Image Computing and Computer-Assisted Intervention—MICCAI; vol. 2. 132-140 (2013), and incorporated by reference in its entirety, a technique of respiratory motion correction in free-breathing sequences was proposed. Specifically, the technique used an iterative registration method based on principal component analysis to compensate for the breathing movements of the patient. However, the resulting peristaltic activity maps that were created provided only qualitative information, rather than an objective measurement of the intestinal activity, e.g. in millimeters per second. Moreover, the proposed technique of Hamy did not provide any structural information of the bowel.

Farghal et al. proposed a method "Developing a new measure of small bowel peristalsis with dynamic MR: a proof of concept study", Acta-Radiologica vol. 53 593-600 (2012), and incorporated by reference in its entirety, to estimate a parametric map for small bowel peristalsis in breath-hold dynamic MR images. The method estimated the motility of the small bowel by means of the mean change in signal amplitude. However, the method of Farghal did not describe or consider any structural information of the bowel.

Additionally, Schuffler et al., proposed a technique based on magnetic resonance imaging in "A Model Development Pipeline for Crohn's Disease Severity Assessment from Magnetic Resonance Images", MICCAI Workshop on Abdominal Imaging: Computational Challenges and Clinical Applications, (2013), and incorporated by reference in its entirety, to assess the severity of Crohn's disease in the intestinal tract. The proposed technique employed machine learning approaches to quantify disease severity. However, the predictive features were manually defined by the clinical expert, and the use of dynamic MRI sequences was not described or considered. Furthermore, the motility of the small bowel was not considered as a predictive feature.

Furthermore, in the work of Froechlich J. M., et al. "MR motility imaging in Crohn's disease improves lesion detection compared with standard MR imaging," Gastrointestinal, 20 (8), 2010, incorporated by reference in its entirety, and the work of Menys, A., et al. "Quantified terminal ideal motility during MR enterography as a potential biomarker of Crohn's disease activity: a preliminary study," Gastrointestinal, 22(11), 2012, and incorporated herein by reference in its entirety, it has been shown that motility (peristaltic activity) of the small bowel correlates with the severity of inflammatory bowel disease.

Accordingly, there is a requirement for assessing and characterizing inflammatory bowel disease by merging and quantifying anatomical and structural information of the small bowel with the quantification of peristaltic activity in order to facilitate accurate and objective diagnosis, monitor efficacy of treatment, evaluate new medical therapies, and thus ensure more directed treatment in inflammatory bowel disease.

SUMMARY

The present disclosure provides for an image processing device and a corresponding method that provides for an imaging biomarker used for the diagnosis, treatment and planning (follow up) of patients with inflammatory bowel diseases. Specifically, the technique for diagnosing bowel diseases as described by the present disclosure, merges information provided by two magnetic resonance enterography (MRE) sequences and creates a set of images that allow the physician/expert to simultaneously analyze the quantitative peristaltic activity extracted from a first MRE sequence (such as fast imaging employing steady-state acquisition, FIESTA) along with the patient's structural details provided by a second MRE sequence (such as single-shot fast spin echo, SSFSE).

According to one embodiment, the image processing device obtains the MRE sequences of a patient as inputs and compensates for the breathing motion in the first MRE sequence (or equivalent). The peristaltic activity is quantified to create a personalized activity map of the small bowel. Further, using multimodal image fusion, based on a similarity measure, the intestinal activity map is merged/fused with the structural information imaging provided by the second MRE sequence (or equivalent), thus creating a new image and biomarkers that provide structural and functional information of the patient in a simultaneous fashion. The fusion and quantification of the two MRE sequences is of great relevance for the diagnosis (and treatment) of inflammatory bowel diseases.

Accordingly, one embodiment of the present disclosure provides for an image processing device for assessing inflammatory bowel disease based on magnetic resonance imaging (MRI). The image processing device includes processing circuitry that is configured to receive, a plurality of dynamic MRI sequence of images of a bowel of a patient, each MRI sequence of images including peristalsis information of the bowel, and receive at least one static MRI image of the bowel of the patient, wherein the static MRI image identifies at least one of areas of inflammation, stenosis, and increased mural thickness of the bowel. The processing circuitry is further configured to compensate for a displacement of the bowel caused by respiration of the patient, by performing a non-rigid registration for each dynamic MRI sequence of images, compute, for each dynamic MRI sequence of images, a peristaltic activity map by performing motion analysis on the MRI sequence of images, determine a peristaltic activity for the at least one static MRI image based on a weighted sum of two closest dynamic MRI sequences of images, the two closest dynamic MRI sequences being determined based on a similarity measure of the static MRI image and the plurality of dynamic MRI sequences of images, and combine the static MRI image and the closest dynamic MRI sequence of images by performing multi-modal registration of the static MRI image and a reference image of the closest dynamic MRI sequences of images.

According to one embodiment is provided a method for assessing inflammatory bowel disease based on magnetic resonance imaging (MRI). The method includes: receiving, a plurality of dynamic MRI sequence of images of a bowel of a patient, each MRI sequence of images including peristalsis information of the bowel and receiving at least one static MRI image of the bowel of the patient, wherein the static MRI image identifies at least one of areas of inflammation, stenosis, and increased mural thickness of the bowel. The method also includes compensating for a displacement of the bowel caused by respiration of the patient, by performing a non-rigid registration for each dynamic MRI sequence of images; computing, for each dynamic MRI sequence of images, a peristaltic activity map by performing motion analysis on the MRI sequence of images determining a peristaltic activity for the at least one static MRI image based on a weighted sum of two closest dynamic MRI sequences of images, the two closest dynamic MRI sequences being determined based on a similarity measure of the static MRI image and the plurality of dynamic MRI sequences of images; and combining the static MRI image and the closest dynamic MRI sequence of images by performing multi-modal registration of the static MRI image and a reference image of the closest dynamic MRI sequences of images.

According to one embodiment of the present disclosure is provided a non-transitory computer readable medium having stored thereon a program that when executed by a computer causes the computer to execute a method that includes: receiving, a plurality of dynamic MRI sequence of images of a bowel of a patient, each MRI sequence of images including peristalsis information of the bowel and receiving at least one static MRI image of the bowel of the patient, wherein the static MRI image identifies at least one of areas of inflammation, stenosis, and increased mural thickness of the bowel. The method also includes compensating for a displacement of the bowel caused by respiration of the patient, by performing a non-rigid registration for each dynamic MRI sequence of images; computing, for each dynamic MRI sequence of images, a peristaltic activity map by performing motion analysis on the MRI sequence of images determining a peristaltic activity for the at least one static MRI image based on a weighted sum of two closest dynamic MRI sequences of images, the two closest dynamic MRI sequences being determined based on a similarity measure of the static MRI image and the plurality of dynamic MRI sequences of images; and combining the static MRI image and the closest dynamic MRI sequence of images by performing multi-modal registration of the static MRI image and a reference image of the closest dynamic MRI sequences of images.

The foregoing paragraphs have been provided by way of general introduction, and are not intended to limit the scope of the following claims. The described embodiments together, with further advantages, will be best understood by reference to the following detailed description taken in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various embodiments of this disclosure that are provided as examples will be described in detail with reference to the following figures, wherein like numerals reference like elements, and wherein.

DETAILED DESCRIPTION OF EMBODIMENTS

Inflammatory bowel diseases such as Crohn's disease typically manifests in the lower part of the small bowel and the colon, with the former involved in 80% of the diagnosed cases. While traditional colonoscopy techniques allow access and diagnosis to the colon, the small bowel is especially difficult to diagnose due to poor access and complex anatomy. According to one embodiment, the development and clinical implementation of optimized magnetic resonance imaging protocols that include MRE is employed in the evaluation of small bowel diseases. Due to its non-invasive nature and the absence of ionizing radiation, MRE is useful in pediatric applications and also for patients who require serial imaging.

Figure 1:
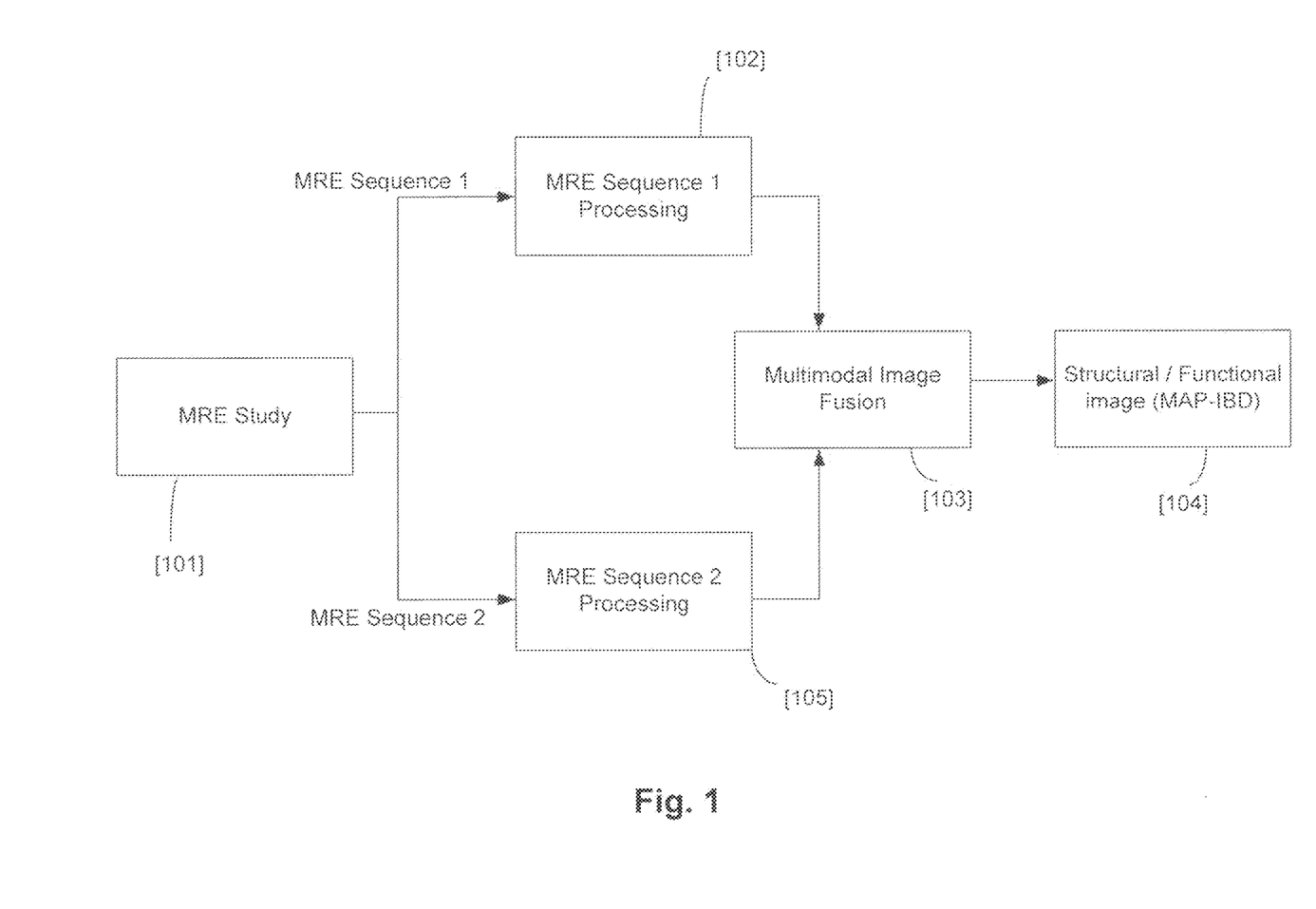
FIG. 1 illustrates according to an embodiment, a flow diagram depicting the steps performed for management, assessment and treatment planning for inflammatory bowel disease (MAP-IBD)

FIG. 1 illustrates according to an embodiment, a flow diagram depicting the steps performed for management, assessment and treatment planning for inflammatory bowel disease (MAP-IBD).

According to one embodiment, two fast sequences of images are acquired in the study of the inflammatory bowel diseases by MRE. The sequences provide sharp images of the anatomy of the intestines. A first MRE sequence, for instance, a Fast-Imaging-Employing-Steady-State-Acquisition (FIESTA) sequence, is a free-breathing sequence in which a single volume of the abdomen is continuously imaged over a predetermined time-period (of the order of several seconds). The first MRE sequence provisions for the monitoring and quantification of the peristalsis activity (defined herein as radially symmetrical contraction and relaxation of a muscle) of the small bowel.

Although, the use of the first MRE sequence (such as the FIESTA sequence) improves lesion and inflammation detection, the presence of black boundary artifacts along the bowel wall may mask small lesions or abnormalities. Therefore, according to one embodiment, a second MRE sequence, such as a Single-Shot Fast Spin Echo (SSFSE) sequence is also used in the diagnosis of bowel diseases. The second MRE sequence is an ultrafast sequence that enables the acquisition of the entire MR data in a single radio frequency excitation. Specifically, the second MRE sequence such as the static SSFSE image sequence provisions for the identification of areas with increased mural thickness frequently associated with bowel sections affected by Crohn's disease.

Turning to FIG. 1, in MRE study 101, dynamic magnetic resonance images (MRE sequence 1 and MRE sequence 2) such as Fast Imaging Employing Steady-State Acquisition (FIESTA) and Single-Shot Fast Spin Echo (SSFSE) sequences or their equivalents are generated. The generated MRE sequence 1 (e.g., the FIESTA sequence) is processed in MRE sequence 1 processing 102, to generate the quantitative peristaltic activity map of the small bowel. The processing of the MRE sequence 1 in 102 includes a breathing compensation stage which allows for both, free-breathing and breath-hold sequences to be used as inputs. Details regarding the processing of MRE sequence 1 are described later with reference to FIG. 2.

The generated MRE sequence 2 (such as a SSFSE sequence) is further processed in MRE sequence 2 processing 105. According to one embodiment, the processing of the MRE sequence 2 in 105 includes quantifying the magnitude of inflammation, determining the amount of distension of the bowel, determining stenosis of the bowel, wall thickness and like. Upon processing the respective MRE sequences in 102 and 105, the MRE sequences are input to a multi-modal image fusion 103.

In multi-modal image fusion 103, the quantitative peristaltic activity map information (obtained for instance, from the FIESTA sequence processing) is fused with the structural and quantitative information obtained for instance, from the SSFSE sequence in order to generate fused structural-functional image.

The structural-functional image 104 provisions for the ability to simultaneously study and quantify the structural information along with the peristaltic activity of a patient in a single image. In addition, the fused image provides imaging biomarkers (defined herein as a measurable indicator of a biological or anatomical state or condition) for inflammatory bowel diseases. An example of a fused image along with biomarkers is described later with reference to FIG. 5.

Figure 2:
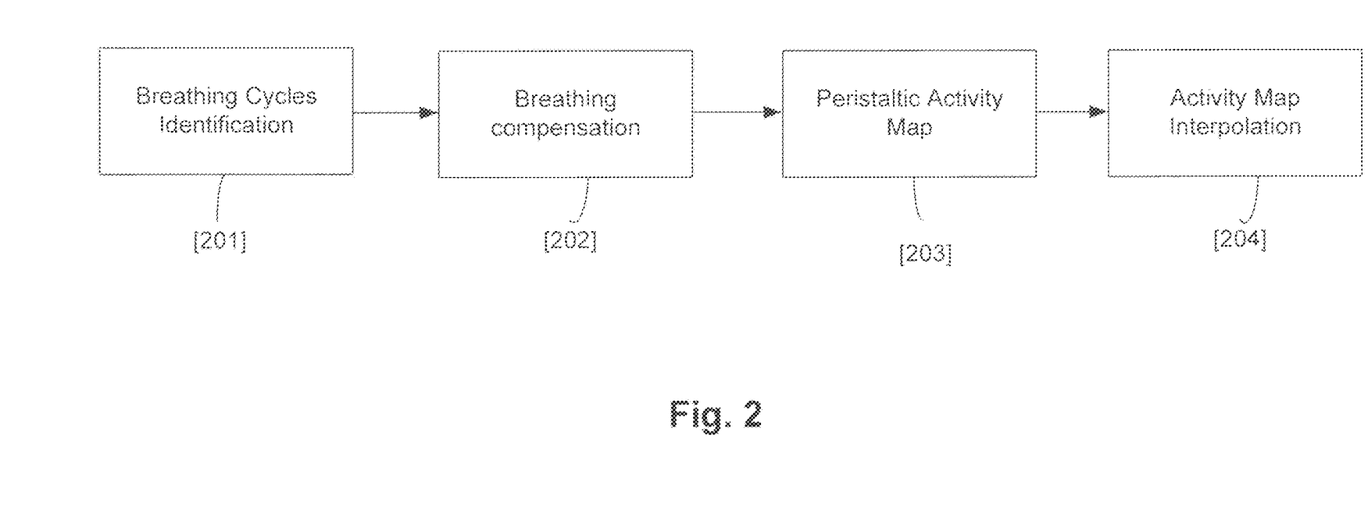
FIG. 2 is a schematic representation of a flow diagram depicting the steps executed in MRE sequence processing, such as FIESTA sequence processing.

FIG. 2 depicts according to one embodiment, a schematic representation of a flow diagram depicting the steps executed in a FIESTA sequence processing. The FIESTA sequence processing compensates for movements of the small bowel caused by respiratory breathing cycles. In what follows, the generation of the peristaltic activity maps is described with reference to stages 201-204 of FIG. 2.

Figure 3:
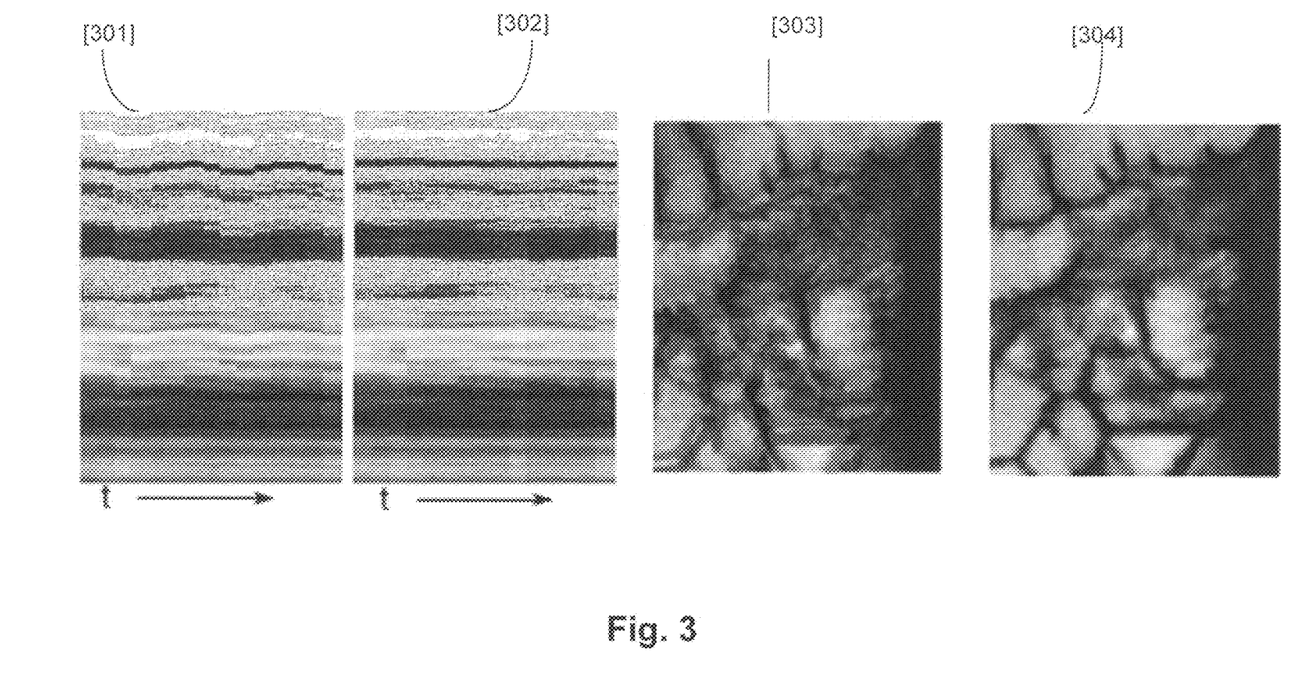
FIG. 3 depicts an exemplary example illustrating the operation of a breathing compensation.

In the step of identification of breathing cycles 201, the image processing device identifies the phase of the respiratory cycle corresponding to each frame of the FIESTA sequence. According to an embodiment, the effects of the respiratory cycle in the sequence of images can be observed graphically by concatenating the horizontal intensity projection of each frame, as depicted in portion 301 of FIG. 3. In FIG. 3, 301 depicts the horizontal intensity projection over time of the original set of frames provided by a free-breathing FIESTA sequence. The arrow marks the middle of the respiratory cycle. In doing so, the image processing device is configured to identify frames that lie in the middle of a breathing cycle. Note that these frames minimize the average frame-to-frame distance, and thus minimize the required deformations to compensate for the breathing effect. Furthermore, as described later, these images are then used as references in the subsequent breathing compensation stage.

In the step of breathing compensation 202, once the frame in the middle of the breathing cycle has been identified as the reference frame, non-rigid registration is performed to compensate the breathing effect. According to one embodiment, non-rigid registration techniques, such as B-splines, can be employed that allow the image processing device to compensate the respiratory displacements that affect the entire abdomen without introducing spurious local deformations that could alter the actual peristalsis information. Thus, non-rigid registration is performed for each FIESTA image frame in each FIESTA sequence.

Alternatively, according to another embodiment, a two-pass registration process can be performed that includes: a first order registration, such as B-spline based, followed by a higher degree B-spline registration (e.g., second order B-spline). Performing multiple levels of registration provides a better compensation of respiratory movements, at a minimal increase in computation time. The horizontal intensity projection over time, of the registered frame sequences (i.e., frames wherein the breathing compensation is achieved) is depicted in FIG. 3, portion 302. Further, in FIG. 3, portion 303 depicts the difference between two frames of the original unregistered sequence wherein gray regions show where the two frames have the same intensities, while colored areas show where the intensities are different. It can be observed that the motility of the small bowel is affected by the general respiratory motion in the abdomen if no breathing compensation is applied. Additionally, in FIG. 3, portion 304 depicts the difference between the frames once the respiratory motion has been compensated, thereby displaying only the bowel motility in the compensated image.

Figure 4:
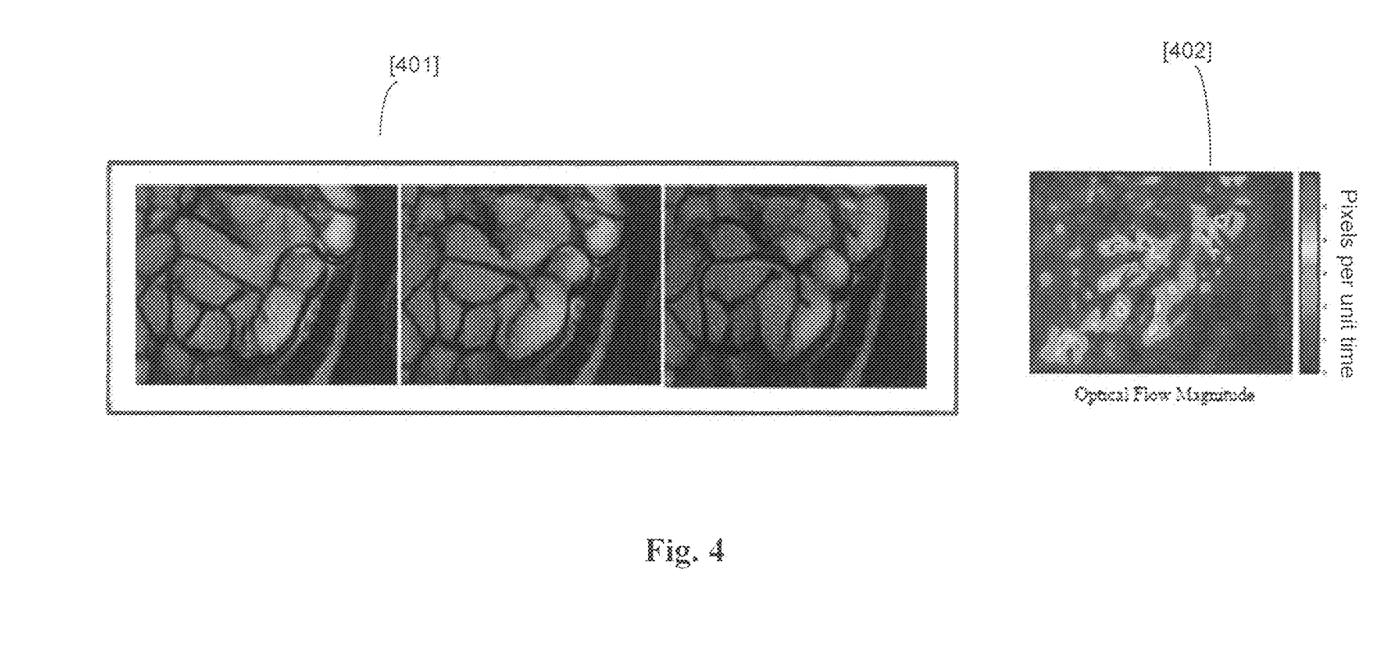
FIG. 4 depicts an exemplary example illustrating peristalsis motion analysis.

Turning to FIG. 2, in step 203 a peristaltic activity map is generated. Specifically, according to one embodiment, once the breathing motion has been compensated, the remaining pattern of apparent motion (i.e., the peristalsis of the bowel) is generated from the sequence of ordered images via motion analysis, such as optical flow analysis. Alternatively, according to one embodiment, the differential-based optical flow approach as described by Horn et al. in "Determining Optical Flow", Artificial Intelligence, 17, 185-203, 1981, and incorporated herein by reference in its entirety, can be used to model the deformation of the small bowel as flow patterns (i.e., a vector field whose components represent the local image flow at each pixel). For instance, as shown in FIG. 4, portion 401 depicts three consecutive registered image frames from the FIESTA sequence illustrating the peristalsis of a particular section of the small bowel. The average optical flow magnitude is shown in 402, thus providing a compact graphical representation of the activity in each bowel area. Note that in 402, the red color represents areas with high motility, while the regions with reduced activity are shown in dark blue. Finally, the process in step 203, accesses the meta-information contained in the input imaging files (i.e., pixel resolution and acquisition time) in order to provide objective units for the motility activity in millimeters per second, as described later with reference to FIG. 5. Thus, the peristaltic activity map is generated based on motion analysis of each of the frames in the FIESTA sequence.

Figure 5:
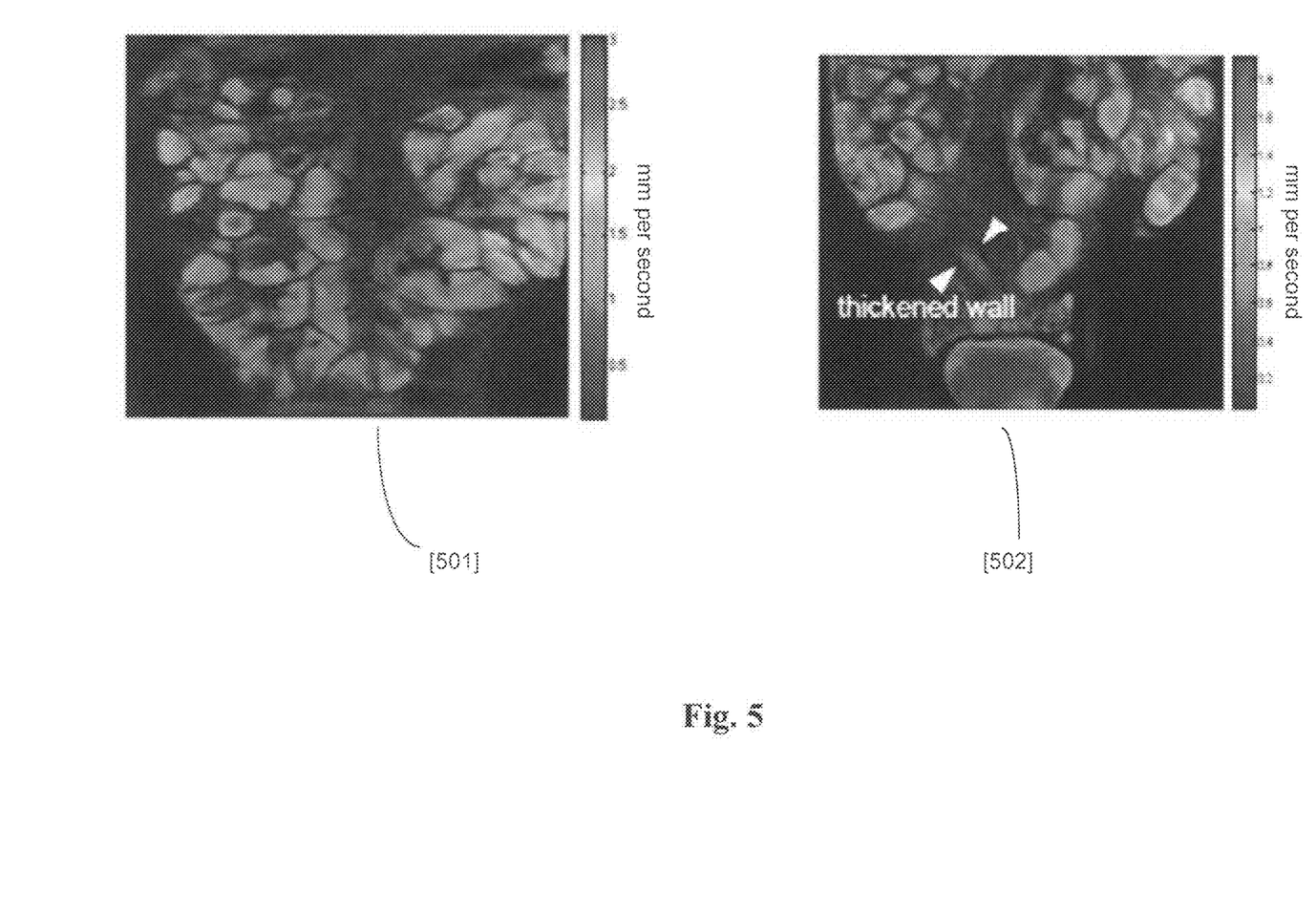
FIG. 5 depicts an exemplary fused image that combines anatomical and functional information.

Although the MRE protocol can be configured to acquire both the FIESTA sequence and the SSFSE image at the same position of the sagittal axis, it is generally not the case in clinical practice. Thus, the method of assessing and treating bowel diseases as described herein includes an activity map interpolation stage 204, in FIG. 2 that allows the SSFSE image to be matched to an activity map derived from a FIESTA sequence. This can be accomplished in one embodiment by identifying the two FIESTA sequences which are close in location to the location where each SSFSE frame was captured. Once the corresponding FIESTA sequences have been identified, the method estimates the specific peristaltic activity for each SSFSE image as a weighted sum of these two nearest activity maps derived from the two closest FIESTA sequences. In one embodiment, the system checks the meta-information contained in the input file(s) corresponding to the FIESTA sequences looking for the spatial location of each image. If this information is available, the mapping between both closest FIESTA sequences and the generation of the final interpolated activity map is done based on the spatial proximity of the image frames in each of the two FIESTA sequences. If the spatial information is not available or the two FIESTA sequences were not acquired in the same spatial coordinates, the method of FIG. 2 may incorporate an alternative approach in a second embodiment that is based on a multi-modal similarity measure. For instance, according to one embodiment, multi-modal similarity is the regularized normalized gradient field proposed by Herber et al. in "Beyond Mutual Information: A Simple and Robust Alternative", Bildverarbeitung fur die Medizin 2005, Informatik Aktuell. Springer Berlin, Heidelberg, 350-354, 2005, and incorporated herein by reference in its entirety. The technique of Herber can also be used to define both the similarity between images from the SSFSE and the FIESTA sequence, as well as being used to define the relative weights to combine the two closest FIESTA sequences as is noted above. Finally, the image processing device may be configured to perform a multimodal registration of each SSFSE image to the final interpolated activity map corresponding to the reference frame in the closest FIESTA sequence, i.e., the one in the middle of the breathing cycle detecting as described previously with respect to FIG. 2, portion 201. The registration allows compensating for possible misalignments between images and fuses both sources of information (the SSFSE image and the FIESTA sequence) into a single new image as depicted in FIG. 5 for a specific location. Specifically, in FIG. 5, 501 depicts the fused image of a healthy patient without bowel inflammation and healthy motility, whereas 502 depicts the fused image of a patient with significant bowel wall thickening (marked with arrows as visible in SSFSE) and reduced motility (as quantified in FIESTA).

Therefore to summarize the method of treating and accessing bowel disease as described above, includes at least one of the following characteristics: (a) breathing compensation to remove breathing motion from the quantification of bowel motility, wherein the inclusion of the breathing compensation stage provisions for a broad spectrum of patients, including those for which a breath-hold study is not feasible, like infants and patients with severe illness, (b) creation of a personalized intestinal activity map that reflects intestinal motility in absolute units of millimeters per second, (c) interpolation stage to create a continuous motility field throughout the entire imaging volume, (d) fusion of functional and structural information via multimodal image registration, and (e) personalized motility scale, allowing to study the intestinal motility in absolute or relative (patient-centered) units for identified healthy and diseased (e.g. with inflammation) areas of the bowels.

Additionally, the technique of assessing bowel diseases has the potential to impact the clinical management of inflammatory bowel diseases at least in the following stages: a) performing quantitative analysis of the bowels from medical imaging, such as magnetic resonance imaging, b) providing virtual access and virtual pathological evaluations to anatomical areas in the abdomen that are difficult, if not impossible to access, e.g. proximal small bowel, c) reducing the subjectivity and variability in the interpretation of diagnostic images for the diagnosis and treatment planning and evaluation of inflammatory bowel diseases, and d) creation of new quantitative imaging biomarkers that facilitate the accurate and objective longitudinal follow up of patients, their enhanced management, and assessment of the response to treatment.

Figure 6:
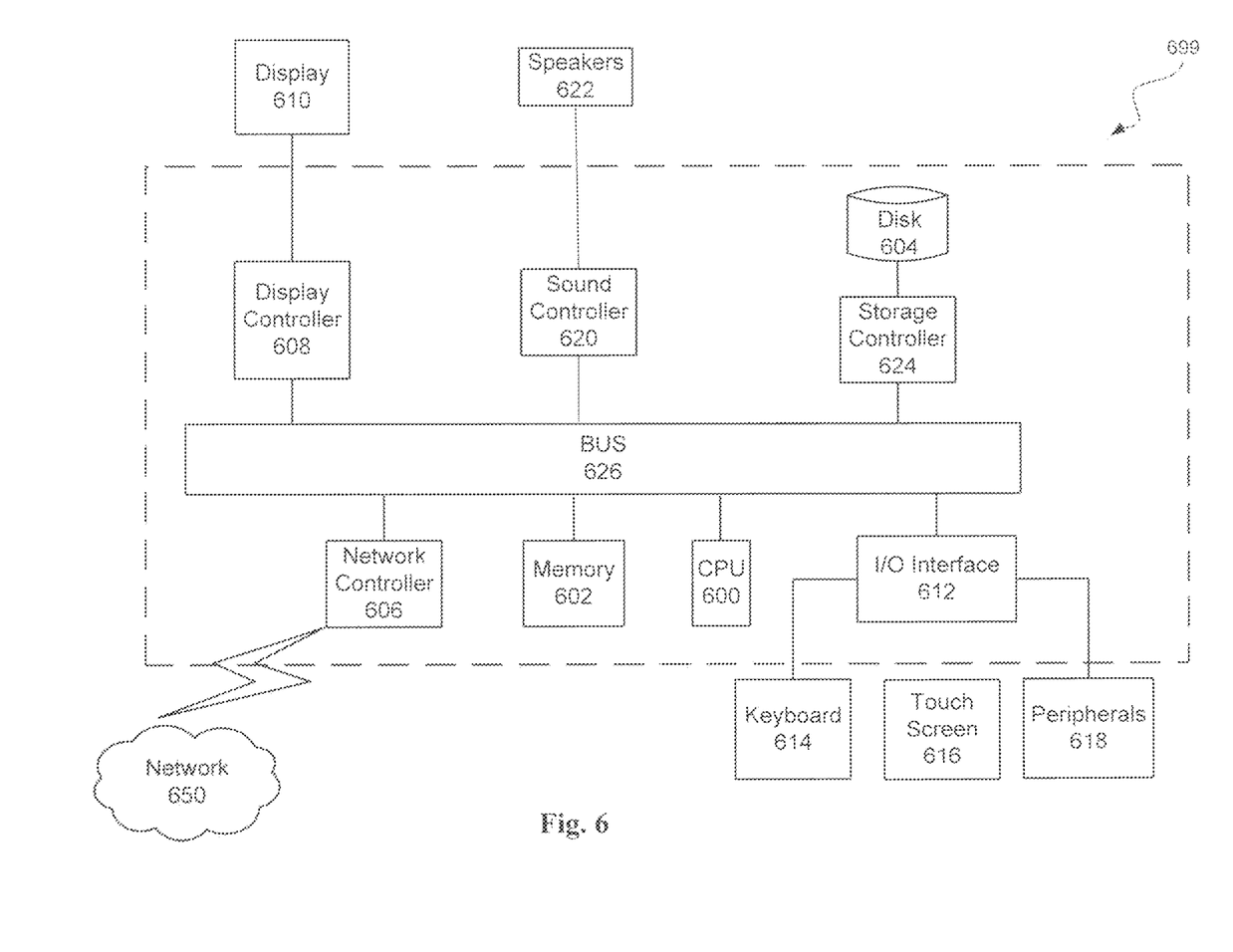
FIG. 6 illustrates a block diagram of a computing device according to one embodiment.

Each of the functions of the above described embodiments may be implemented by a control circuitry, which includes one or more processing circuits. A processing circuit includes a programmed processor, for example, processor (CPU) 600, as shown in FIG. 6. A processing circuit also includes devices such as an application specific integrated circuit (ASIC) and conventional circuit components arranged to perform the recited functions.

In FIG. 6, the computer 699 includes a CPU 600 which performs the processes described above. The process data and instructions may be stored in memory 602. These processes and instructions may also be stored on a storage medium disk 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the system communicates, such as a server or computer.

Further, the claimed advancements may be provided as a utility application, background daemon, or component of an operating system, or combination thereof, executing in conjunction with CPU 600 and an operating system such as Microsoft Windows 7, UNIX, Solaris, LINUX, Apple MAC-OS and other systems known to those skilled in the art.

CPU 600 may be a Xenon or Core processor from Intel of America or an Opteron processor from AMD of America, or may be other processor types that would be recognized by one of ordinary skill in the art. Alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the inventive processes described above.

The computer 699 in FIG. 6 also includes a network controller 606, such as an Intel Ethernet PRO network interface card from Intel Corporation of America, for interfacing with network 650. As can be appreciated, the network 650 can be a public network, such as the Internet, or a private network such as an LAN or WAN network, or any combination thereof and can also include PSTN or ISDN sub-networks. The network 650 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer 699 further includes a display controller 608, such as a NVIDIA GeForce GTX or Quadro graphics adaptor from NVIDIA Corporation of America for interfacing with display 610, such as a Hewlett Packard HPL2445w LCD monitor. A general purpose I/O interface 612 interfaces with a keyboard and/or mouse 614 as well as a touch screen panel 616 on or separate from display 610. General purpose I/O interface also connects to a variety of peripherals 618 including printers and scanners, such as an OfficeJet or DeskJet from Hewlett Packard. The peripheral elements previously described in the above exemplary embodiments may be embodied by the peripherals 618 in the exemplary embodiments.

A sound controller 620 may also be provided in the computer 699, such as Sound Blaster X-Fi Titanium from Creative, to interface with speakers/microphone 622 thereby providing sounds and/or music. The speakers/microphone 622 can also be used to accept dictated words as commands for controlling the robot-guided medical procedure system or for providing location and/or property information with respect to the target property.

The general purpose storage controller 624 connects the storage medium disk 604 with communication bus 626, which may be an ISA, EISA, VESA, PCI, or similar, for interconnecting all of the components of the robot-guided medical procedure system. A description of the general features and functionality of the display 610, keyboard and/or mouse 614, as well as the display controller 608, storage controller 624, network controller 606, sound controller 620, and general purpose I/O interface 612 is omitted herein for brevity as these features are known.

Obviously, numerous modifications and variations of the present disclosure are possible in light of the above teachings. It is therefore to be understood that within the scope of the appended claims, the invention may be practiced otherwise than as specifically described herein. For example, advantageous results may be achieved if the steps of the disclosed techniques were performed in a different sequence, if components in the disclosed systems were combined in a different manner, or if the components were replaced or supplemented by other components. For example, certain of the above described techniques and processes could be applied to other parts of the body in addition to the gastrointestinal tract, for example, to identify the inflammation and motion, fuse multi-modal and multi-sequence images, quantify structure and function or to identify and address other medical issues.

The functions, processes and algorithms described herein may be performed in hardware or software executed by hardware, including computer processors and/or programmable processing circuits configured to execute program code and/or computer instructions to execute the functions, processes and algorithms described herein. A processing circuit includes a programmed processor, as a processor includes circuitry. A processing circuit also includes devices such as an application specific integrated circuit (ASIC) and conventional circuit components arranged to perform the recited functions.

The functions and features described herein may also be executed by various distributed components of a system. For example, one or more processors may execute these system functions, wherein the processors are distributed across multiple components communicating in a network. The distributed components may include one or more client and/or server machines, in addition to various human interface and/or communication devices (e.g., display monitors, smart phones, tablets, personal digital assistants (PDAs)). The network may be a private network, such as a LAN or WAN, or may be a public network, such as the Internet. Input to the system may be received via direct user input and/or received remotely either in real-time or as a batch process. Additionally, some implementations may be performed on modules or hardware not identical to those described. Accordingly, other implementations are within the scope that may be claimed.

It should be noted that, as used in the specification and the appended claims, the singular forms "a," "an," and "the" include plural referents unless the context clearly dictates otherwise.

It should also be noted the FIESTA sequences are one exemplary way of obtaining peristalsis information of the bowel. In addition, SSFSE images are one way of obtaining structural information of the bowel. Further, the present technique could be used for other portions of the body.

What is claimed is:

1. An image processing device for assessing inflammatory bowel disease based on MRI images, the device comprising: circuitry configured to receive, a first sequence of MRI images of a bowel of a patient, each MRI image included in the first sequence of MRI images including peristalsis information of the bowel, receive at least one static MRI image of the bowel of the patient, wherein the static MRI image provides anatomical and structural information that identifies areas of inflammation, stenosis, and increased mural thickness of the bowel, compensate for a displacement of the bowel caused by respiration of the patient, by performing a registration, based on a reference image, for each image of the first sequence of MRI images, the reference image corresponding to a central midpoint of a breathing cycle of the patient, compute, for each image of the first sequence of MRI images, a corresponding peristaltic activity map by performing motion analysis on the first sequence of MRI images, compute a peristaltic activity map for the at least one static MRI image based on a weighted sum of two closest MRI sets of images of the first sequence of MRI images, the two closest MRI sets being determined based on a similarity measure of the at least one static MRI image and the first sequence of MRI images, and assess inflammation of the bowel by generating a new fused image by combining the at least one static MRI image and the computed peristaltic activity map for the at least one static MRI image interpolated, based on the weighted sum, from the two closest MRI sets of images from the first sequence of MRI images.

2. The image processing device of claim 1, wherein the first sequence of MRI images is a cine steady-state free precision sequence and the at least one static MRI image is a single-shot sequence.

3. The image processing device of claim 2, wherein the first sequence of MRI images includes images corresponding to a free-breathing cycle of the patient or a breath-hold cycle of the patient.

4. The image processing device of claim 1, wherein the generated fused image includes bio-markers that indicate portions of the bowel of the patient and a corresponding motility.

5. The image processing device of claim 1, wherein the circuitry is further configured to identify, for each image of the first sequence of MRI images, a phase of the breathing cycle of the patient.

6. The image processing apparatus of claim 1, wherein the registration is a non-rigid registration using the reference image.

7. The image processing apparatus of claim 1, the motion analysis is an optical flow analysis process.

8. A method for assessing inflammatory bowel disease based on MRI images, the method comprising:

receiving a first sequence of MRI images of a bowel of a patient, each MRI image included in the first sequence of MRI images including peristalsis information of the bowel, receiving at least one static MRI image of the bowel of the patient, wherein the static MRI image provides anatomical and structural information that identifies areas of inflammation, stenosis, and increased mural thickness of the bowel, compensating for a displacement of the bowel caused by respiration of the patient, by performing a registration, based on a reference image, for each image of the first sequence of MRI images, the reference image corresponding to a central midpoint of a breathing cycle of the patient, computing by circuitry, for each image of the first sequence of MRI images, a corresponding peristaltic activity map by performing motion analysis on the first sequence of MRI images, computing by the circuitry, a peristaltic activity map for the at least one static MRI image based on a weighted sum of two closest MRI sets of images of the first sequence of MRI images, the two closest MRI sets being determined based on a similarity measure of the at least one static MRI image and the first sequence of MRI images, and assessing inflammation of the bowel by generating a new fused image by combining the at least one static MRI image and the computed peristaltic activity map for the at least one static MRI image interpolated, based on the weighted sum, from the two closest MRI sets of images from the first sequence of MRI images.

9. The method of claim 8, wherein the generated fused image includes bio-markers that indicate portions of the bowel of the patient and a corresponding motility.

10. The method of claim 9, further comprising:

diagnosing and providing a treatment plan or treatment assessment for the patient based on the bio-markers included in the generated fused image.

11. The method of claim 8, wherein the first sequence of MRI images is a cine steady-state free precision sequence, and the at least one static MRI image is a single-shot sequence.

12. The method of claim 11, wherein the first sequence of MRI images includes images corresponding to a free-breathing cycle of the patient and a breath-hold cycle of the patient.

13. The method of claim 8, further comprising:

identifying by the circuitry, for each image of the first sequence of MRI images, a phase of the breathing cycle of the patient.

14. The method of claim 8, wherein the registration is a non-rigid registration using the reference image.

15. The method of claim 8, wherein the motion analysis is an optical flow analysis process.

16. A non-transitory recording medium including computer executable instructions, wherein the instructions, when executed by a computer, cause the computer to perform a method for assessing inflammatory bowel disease based on MRI images, the method comprising:

receiving a first sequence of MRI images of a bowel of a patient, each MRI image included in the first sequence of MRI images including peristalsis information of the bowel, receiving at least one static MRI image of the bowel of the patient, wherein the static MRI image provides anatomical and structural information that identifies areas of inflammation, stenosis, and increased mural thickness of the bowel, compensating for a displacement of the bowel caused by respiration of the patient, by performing a registration, based on a reference image, for each image of the first sequence of MRI images, the reference image corresponding to a central midpoint of a breathing cycle of the patient, computing, for each image of the first sequence of MRI images, a corresponding peristaltic activity map by performing motion analysis on the first sequence of MRI images, computing a peristaltic activity for the at least one static MRI image based on a weighted sum of two closest MRI sets of images of the first sequence of MRI images, the two closest MRI sets being determined based on a similarity measure of the at least one static MRI image and the first sequence of MRI images, and assessing inflammation of the bowel by generating a new fused image by combining the at least one static MRI image and the computed peristaltic activity map for the at least one static MRI image interpolated, based on the weighted sum, from the two closest MRI sets of images from the first sequence of MRI images.

17. The non-transitory recording medium of claim 16, wherein the first sequence of MRI images is a cine steady-state free precision sequence, and the at least one static MRI image is a single-shot sequence.

18. The non-transitory recording medium of claim 16, wherein the first sequence of MRI images includes images corresponding to a free-breathing cycle of the patient and a breath-hold cycle of the patient.

19. The non-transitory recording medium of claim 16, wherein the generated fused image includes bio-markers that indicate portions of the bowel of the patient and their corresponding motility information.

20. The non-transitory recording medium of claim 16, further comprising:
identifying for each image of the first sequence of MRI images, a phase of the breathing cycle of the patient.

21. The non-transitory recording medium of claim 16, wherein the registration is a non-rigid registration.

22. The non-transitory recording medium of claim 16, wherein the motion analysis is an optical flow analysis process.

23. The non-transitory recording medium of claim 19, further comprising:
diagnosing and providing a treatment plan or treatment assessment for the patient based on the bio-markers included in the generated fused image.

* * * * *